(12) United States Patent
Yao et al.

(10) Patent No.: US 8,501,495 B2
(45) Date of Patent: Aug. 6, 2013

(54) SEQUENTIAL SOLID PHASE IMMUNOASSAY INCLUDING CONTACT PAD TO LIMIT CONJUGATE FLOW DURING MANUFACTURE

(75) Inventors: Kai Ling Yao, Daly City, CA (US); Peter Chun, South San Francisco, CA (US)

(73) Assignee: Equal Access to Scientific Excellence, South San Francisco, CA (US)

( * ) Notice: Subject to any disclaimer, the term of this patent is extended or adjusted under 35 U.S.C. 154(b) by 332 days.

(21) Appl. No.: 12/704,147

(22) Filed: Feb. 11, 2010

(65) Prior Publication Data

US 2010/0144061 A1    Jun. 10, 2010

Related U.S. Application Data

(62) Division of application No. 11/800,364, filed on May 3, 2007, now abandoned.

(51) Int. Cl.
*G01N 33/558* (2006.01)
*G01N 33/563* (2006.01)
*G01N 33/53* (2006.01)
*C12N 1/34* (2006.01)

(52) U.S. Cl.
USPC .......... 436/514; 436/513; 436/530; 436/810; 435/7.1; 435/287.2; 435/287.7

(58) Field of Classification Search
None
See application file for complete search history.

(56) References Cited

U.S. PATENT DOCUMENTS

| | | | | |
|---|---|---|---|---|
| 4,943,522 A * | 7/1990 | Eisinger et al. | | 435/7.25 |
| 4,981,786 A * | 1/1991 | Dafforn et al. | | 435/7.92 |
| 5,340,748 A * | 8/1994 | Baugher et al. | | 436/518 |
| 5,468,648 A * | 11/1995 | Chandler | | 436/518 |
| 5,559,041 A * | 9/1996 | Kang et al. | | 436/518 |
| 5,571,667 A * | 11/1996 | Chu et al. | | 435/5 |
| 5,656,503 A * | 8/1997 | May et al. | | 436/514 |
| 5,726,013 A * | 3/1998 | Clark | | 435/5 |
| 6,406,920 B1 * | 6/2002 | Davis et al. | | 436/518 |
| 6,573,108 B1 * | 6/2003 | Hardman et al. | | 436/518 |
| 6,686,167 B2 * | 2/2004 | Bagaria | | 435/7.2 |
| 6,699,722 B2 * | 3/2004 | Bauer et al. | | 436/518 |
| 6,818,455 B2 * | 11/2004 | May et al. | | 436/514 |
| 7,919,331 B2 * | 4/2011 | Geisberg | | 436/514 |
| 7,972,871 B2 * | 7/2011 | Chandler | | 436/514 |

(Continued)

FOREIGN PATENT DOCUMENTS

CN    1740794    * 3/2006

*Primary Examiner* — Shafiqul Haq
*Assistant Examiner* — Gary E Hollinden
(74) *Attorney, Agent, or Firm* — James Cai; Schein & Cai LLP

(57) ABSTRACT

A sequential solid phase immunoassay and system is disclosed. The immunoassay utilizes the secondary antibody method for the detection of antibodies in a membrane-based test. The system comprises a test strip including a nitrocellulose membrane having an immobilized antigen in a capture zone on the membrane and a stabilized liquid secondary antibody conjugate. The sequential solid phase immunoassay is performed in a sequential manner with the addition of a fluid specimen being followed by the addition of the stabilized liquid secondary antibody conjugate. The sequential procedure using the system includes allowing the fluid specimen containing antibodies specific to the antigen to pass laterally from the test strip first end through the capture zone. The immobilized antigens in the capture zone capture antibodies specific to the antigen. The stabilized liquid secondary antibody conjugate then binds to the captured antibodies and can be detected visually or by a machine or reader.

2 Claims, 5 Drawing Sheets

U.S. PATENT DOCUMENTS

| | | | |
|---|---|---|---|
| 2003/0219908 A1* | 11/2003 | Davis et al. | 436/514 |
| 2004/0023412 A1* | 2/2004 | Carlsson et al. | 436/514 |
| 2004/0137641 A1* | 7/2004 | Holtlund et al. | 436/514 |
| 2004/0219690 A1* | 11/2004 | Choi et al. | 436/514 |
| 2004/0235189 A1* | 11/2004 | Lu | 436/514 |
| 2004/0241879 A1* | 12/2004 | Robinson | 436/514 |
| 2006/0134802 A1* | 6/2006 | Donati et al. | 436/514 |
| 2006/0134803 A1* | 6/2006 | Esfandiari | 436/514 |
| 2006/0141639 A1* | 6/2006 | Bauer et al. | 436/514 |
| 2006/0166374 A1* | 7/2006 | Hubscher | 436/514 |

* cited by examiner

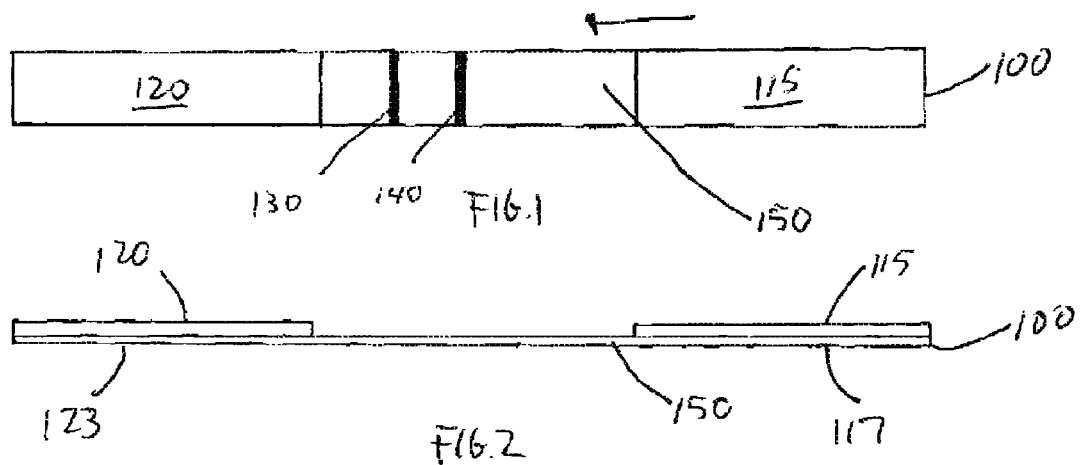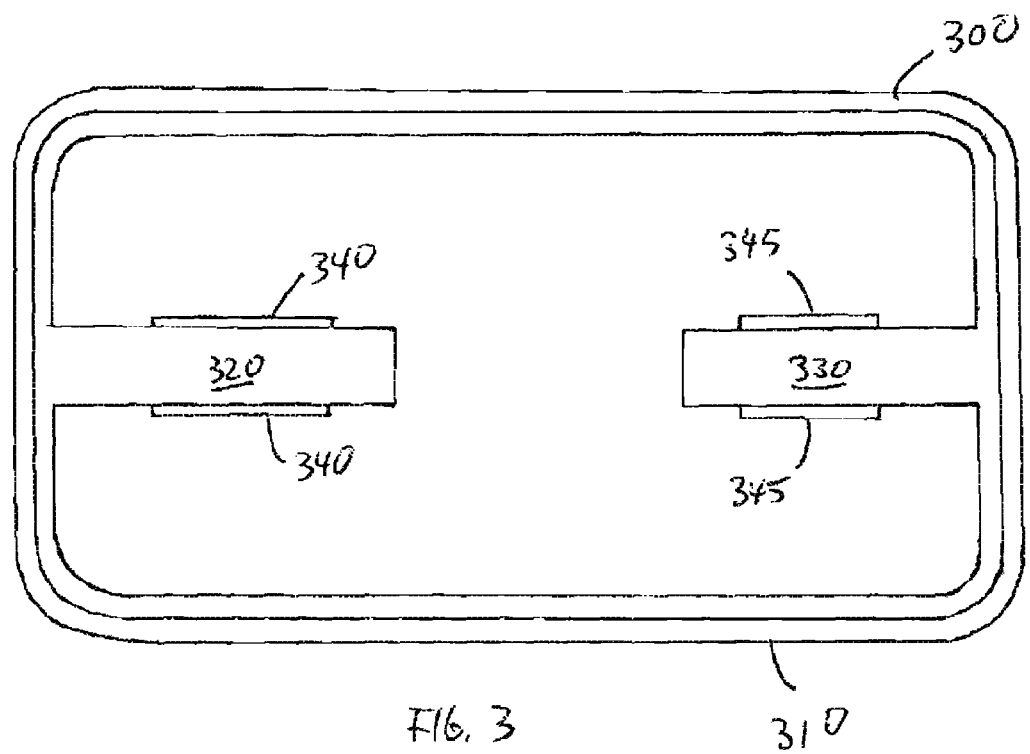

SEQUENTIAL SOLID PHASE IMMUNOASSAY INCLUDING CONTACT PAD TO LIMIT CONJUGATE FLOW DURING MANUFACTURE

CROSS-REFERENCE TO RELATED APPLICATION

The present application is a Divisional of U.S. patent application Ser. No. 11/800,364, filed May 3, 2007 now abandoned.

BACKGROUND OF THE INVENTION

1. Field of the Invention

The present invention relates to immunochromatography and more particularly to sequential solid phase immunoassays and a system used in performing the immunoassays.

2. Description of Related Art

The use of lateral flow immunochromatography along with colloidal dye conjugates is well known in the field of rapid diagnostics. Various diagnostic kits have been developed and marketed based on these methods. In principle, a specific member of a combining pair (an antigen or an antibody, for example) is immobilized onto a specific capture zone in one of many different kinds of membranes, such as nitrocellulose. As a fluid sample containing the complementary member of the combining pair (complementary antigen or antibody) passes through the capture zone, it is captured by the immobilized member. Another biological reagent, which also specifically binds to the captured member, is conjugated to one of a number of colored particles such as colloidal gold and is used to visualize the captured member. Frequently the colored particle conjugate is in dry form and strategically placed between the capture zone and the sample application zone and in the path of sample flow, so that the fluid sample can reconstitute the conjugate and react with it before reaching the capture zone.

For the detection of antigens, this represents a rather straight-forward method in which the capture zone contains immobilized antibodies (A) specific for the antigen and the conjugate contains specific antibodies (B). At the capture zone, the antigen is essentially sandwiched between two antibodies; one immobilized on the membrane and the other on the colored conjugate. This sandwich is easily detected visually or by a reader.

The prior art provides three different general approaches to antibody detection. In the double antigen sandwich method, the antigen is immobilized onto the membrane, and is also conjugated onto the colored particles. The specific antibody in the biological specimen to be detected essentially cross links with the two antigens. The advantages of this method are that it is rapid, sensitive and can be done in one single step, without the need for wash steps. The chief disadvantages of this method are that: 1) it is sometimes difficult to conjugate antigens onto particles as each antigen may have a unique set of conditions in which it needs to be conjugated to retain immunological reactivity and avoid steric hindrance; 2) it is not possible to distinguish between IgG and IgM antibodies, which may be very important in clinical situations (to distinguish between primary and secondary infections); and 3) when the antibody/antigen ratio falls outside of the range of effective formation of immobilized antigen-antibody-conjugated antigen cross-links, the test renders a false negative resulting in decreased sensitivity due to the prozone effect.

In an antibody capture method, specific anti-IgG or anti-IgM (or a combination of both) are immobilized onto the membrane at the capture zone. Antigen is conjugated onto the colored particle. Specific antibodies contained in the biological specimen react and bind with the antigen-colored particle conjugate and as it passes through the capture zone, become captured by the antibodies. The advantages of this method include the fact that IgG and IgM antibodies can be distinguished, and the reaction can be completed as a one step reaction without wash steps. The chief disadvantages are: 1) that conjugation of the antigen could present a challenge as mentioned above with regard to the double antigen method; and 2) that when the specific titer is low (in other words, the specific antibodies' concentrations are low) and the overall IgG or IgM antibody levels are high, the sensitivity may be decreased due to a low ratio of specific to nonspecific antibody levels and to the finite number of capture sites in the capture zone proportionately more occupied by extraneous antibodies. This is because the ratio of specific to nonspecific antibody level is low, and the capture sites of the capture zone which are finite may be proportionately more occupied by extraneous antibodies. This is particularly so in the case of IgG.

In a second antibody method, the antigen is immobilized onto the capture zone of the membrane. The specific antibody contained in the fluid sample is captured by the antigen as the specimen passes through the capture zone. A secondary antibody (specific for IgG or IgM or both) conjugated onto the colored particle is then applied, and as it passes through the capture zone, binds to the captured specific antibodies, thereby being visualized. Using this method, IgG and IgM can be distinguished by the use of different conjugates which are specific for one or the other antibody. Another advantage is that antigens do not need to be conjugated to the colored particles; a universal set of secondary antibodies (anti-IgG or IgM) can be used for many different assays, thus simplifying manufacturing in a commercial setting. When done in a sequential manner, first with the addition of the sample, followed by a wash step to wash away extraneous non-specific antibodies, and then the addition of the conjugate, the method is not subject to being overwhelmed by excessive extraneous antibodies. The chief disadvantage is that one or more wash steps need to be implemented to avoid the exhaustion of the conjugate. If there is too much non-specific antibody in the specimen, it will bind to and exhaust the conjugate, leaving an insufficient amount to bind to the specific antibodies and causing low sensitivity.

U.S. Pat. No. 6,818,455 to May et al. entitled "Capillary Immunoassay and Device Therefor Comprising Mobilizable Particulate Labelled Reagents" discloses an analytical device having an immobilized labeled reagent adjacent a lower end of a test strip. A sample to be tested is added behind the immobilized labeled reagent and reconstitutes the labeled reagent which then moves toward a reaction zone. The disclosed immunoassay suffers the disadvantages mentioned above related to antibody tests and low sensitivity due to the prozone effect related to antigen tests.

US Patent Application Publication No. 2004/0235189 to Lu entitled "Reversed Chromatographic Immunoassay" discloses a chromatographic immunoassay test strip comprising a solid support having a pre-dried immobilized ligand/tracer. In use, a specimen is added ahead of the immobilized ligand B/tracer and a buffer is used to dissolve the ligand B/tracer, facilitate the movement of the sample along the strip, and allow it to react with a binder (ligand A) immobilized in a test region. The buffer may also clean up the strip of bound material outside of the test region. The disclosed immunoassay suffers the disadvantages of requiring a separate buffer and reduced sensitivity due to the relatively limited pre-dried immobilized ligand B/tracer which is insufficient to achieve sensitive detection.

What is needed then is a sequential solid phase immunoassay and system thereof that overcomes the limitations of the prior art. What is further needed is a sequential solid phase immunoassay that utilizes the secondary antibody method for the detection of antibodies in a membrane-based test. What is also needed is a sequential solid phase immunoassay that utilizes stabilized liquid secondary antibody conjugates of sufficient quantity as visualization reagents. What is further needed is a sequential solid phase immunoassay that provides for a fluid specimen added to a fluid specimen application zone distal from a capture zone having an immobilized antigen. What is also needed is a sequential solid phase immunoassay that provides for application of an excess secondary antibody conjugate in the fluid specimen application zone or distal of the fluid specimen application zone, after the fluid specimen is added such that the conjugate flows in the same direction as the fluid specimen and behind the fluid specimen. What is further needed is a sequential solid phase immunoassay that provides a sequential reaction to thereby provide better sensitivity at both a low end and a high end of analyte concentration. What is further needed is a sequential solid phase immunoassay wherein the liquid secondary antibody conjugate serves to wash excess non-specific antibodies and continuously supplies sufficient reactive conjugate material throughout the entire test run time, such that extraneous non-specific antibodies do not overwhelm the system.

SUMMARY OF THE INVENTION

The present invention addresses the needs of the prior art by providing a sequential solid phase immunoassay and system that utilizes the secondary antibody method for the detection of antibodies in a membrane-based test. The system comprises a test strip including a nitrocellulose membrane having an immobilized antigen in a capture zone on the membrane and a stabilized liquid secondary antibody conjugate (liquid conjugate). The test strip has first and second ends, the capture zone being distal of the first end of the test strip. The test strip may be disposed in a housing having a fluid specimen application window and a liquid conjugate application well.

The sequential solid phase immunoassay is performed in a sequential manner with the addition of the fluid specimen being followed by the addition of the liquid conjugate. The sequential procedure using the system includes allowing the fluid specimen containing antibodies specific to the antigen to pass laterally from the test strip first end through the capture zone. The immobilized antigens in the capture zone capture antibodies specific to the antigen. The liquid conjugate then binds to the captured antibodies and can be detected visually or by a machine or reader.

The liquid conjugate provides a stabilized liquid conjugate having an excess of labeled secondary antibody conjugate. The liquid conjugate incorporates buffers, salts, detergents and/or surfactants, and blocking proteins to wash non-specific antibodies along the test strip and to thereby leave a sufficient amount of conjugate in the capture zone to bind to the specific antibodies.

The delivery of the fluid specimen to the capture zone is facilitated in the test strip in several ways. In accordance with an aspect of the invention, the liquid conjugate is effective in pushing from behind the fluid specimen along the test strip. In accordance with another aspect of the invention, the liquid conjugate is effective in carrying the fluid sample along the test strip.

In accordance with another aspect of the invention, a viscous fluid specimen is first mixed with a buffer in a test tube to dilute the fluid specimen. The first end of the test strip is next dipped in the test tube distal of the capture zone. The dilute fluid specimen passes laterally from the first end of the test strip through the capture zone where antibodies specific to the immobilized antigens capture antibodies specific to the antigen. Following having been dipped in the test tube, the first end of the test strip is dipped in the liquid conjugate that passes laterally through the capture zone and binds to the captured antibodies. The captured antibodies can then be detected.

In accordance with another aspect of the invention, a sequential solid phase immunoassay system includes a test strip having a first absorbent material disposed at a first end thereof and a second absorbent material disposed at a second end thereof, and an antigen immobilized on the test strip at a capture zone, the capture zone disposed between the first and second absorbent materials and distally of the first absorbent material, and a stabilized liquid secondary antibody conjugate.

In accordance with yet another aspect of the invention, a sequential solid phase immunoassay includes the steps of: 1) providing a sequential solid phase immunoassay system; 2) applying a fluid specimen to the fluid specimen application zone; 3) applying a stabilized liquid conjugate to the first absorbent material; and 4) reading the results.

In accordance with another aspect of the invention, a sequential solid phase immunoassay includes the steps of: 1) providing a sequential solid phase immunoassay system; 2) applying a stabilized liquid conjugate to the first absorbent material; 3) applying a fluid specimen to the fluid specimen application zone immediately following step 2); and 4) reading the results.

In accordance with yet another aspect of the invention, a sequential solid phase immunoassay includes the steps of: 1) providing a sequential solid phase immunoassay system; 2) diluting a fluid specimen with a buffer or a stabilized liquid conjugate; 3) dipping the test strip in the diluted fluid specimen; 4) dipping the test strip in the stabilized liquid conjugate; and 5) reading the results.

There has been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended herein.

In this respect, before explaining at least one embodiment of the invention in detail, it is to be understood that the invention is not limited in its application to the details of functional components and to the arrangements of these components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein:

FIG. 1 is a top plan view of a sequential solid phase immunoassay test strip in accordance with the invention;

FIG. 2 is a side elevation view of the test strip of FIG. 1;

FIG. 3 is a top plan view of a housing bottom portion in accordance with the invention;

DETAILED DESCRIPTION

Figure 4:
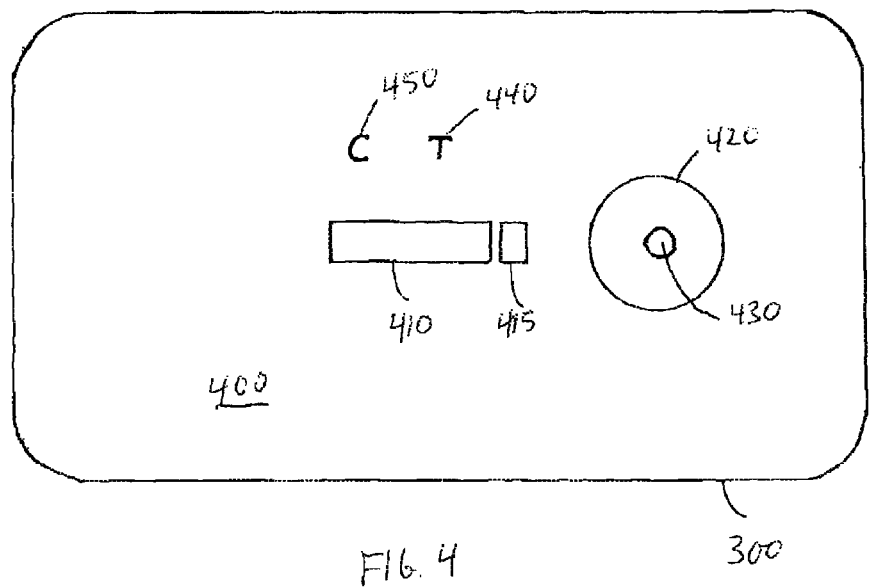
FIG. 4 is a top plan view of a housing top portion in accordance with the invention.

The sequential solid phase immunoassay system of the invention generally comprises a test strip including a nitrocellulose membrane having an immobilized antigen in a capture zone on the membrane and a stabilized liquid secondary antibody conjugate. The test strip may be housed in a housing. The sequential solid phase immunoassay generally comprises procedures for use of the system in the secondary method for the detection of antibodies.

With reference to FIG. 1 and FIG. 2, a sequential chromatographic immunoassay test strip 100 is shown. The test strip 100 is preferably formed of nitrocellulo membrane material. A first absorbent material 115 overlays the test strip 100 at a first end 117 thereof and serves as an application area for the liquid conjugate as further described herein. A second absorbent material 120 overlays the test strip 100 at a second end 123 thereof and serves as a drive for driving liquid movement laterally across the test strip 100 in the direction indicated by the arrow.

A capture zone 140 includes an antigen immobilized on the membrane. A control zone 130 may be provided to provide an indication of the reactivity of the liquid conjugate. A fluid specimen application zone 150 is shown disposed distally of the capture zone 140 proximate the first absorbent material 115.

Figure 5:
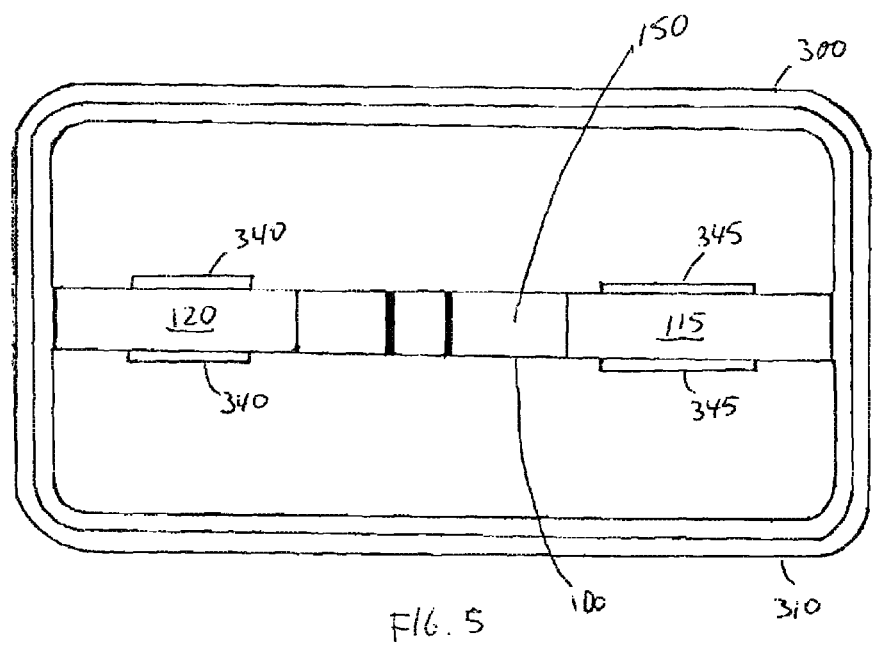
FIG. 5 is a top plan view of the housing bottom portion showing the test strip in place in accordance with the invention.

In accordance with one aspect of the invention, the test strip 100 may be held inside a housing 300 as shown in FIG. 3, FIG. 4, and FIG. 5. Housing 300 may be formed of any suitable material including plastic and includes a top portion 400 and a bottom portion 310 attachable one to the other by conventional means. Housing bottom portion 310 includes a pair of recessed areas 320 and 330 sized and configured to receive the test strip 100 therewithin as shown in FIG. 5. Pairs of lateral ridges 340 and 345 bound recessed areas 320 and 330 respectively and frictionally hold the test strip 100 within the recessed areas. In a preferred embodiment, the lateral ridges 345 and 340 bound the first absorbent material 115 and the second absorbent material 120 respectively.

The housing top portion 400 includes a result viewing window 410, a fluid specimen application window 415, and a liquid conjugate application well 420 having an opening 430 formed at a bottom thereof. Housing top portion 400 further includes indicia 440 and 450 corresponding to the capture zone 140 (labeled "T" for test) and to the control zone 130 (labeled "C" for control) respectively. When the test strip 100 is held in the housing 300, the fluid specimen application window 415 is positioned over the fluid specimen application zone 150.

The liquid conjugate well 420 comprises a depression formed in the housing top portion 400 into which the liquid conjugate is poured. When the test strip 100 is held in the housing 300, the opening 430 is positioned to provide fluid communication of the liquid conjugate with the first absorbent material 115 positioned in underlying relationship with the opening 430.

The stabilized liquid secondary antibody conjugate preferably includes a stabilized liquid secondary antibody-colored particle conjugate. The secondary antibodies include anti-IgG, anti-IgM, and anti-IgA antibodies. Substitution by protein A or Protein G for anti-IgG may be used for the detection of IgG antibodies. Colored particles can be one of many colloidal metal sols, colored latex particles, colloidal carbon and dyes. The stabilized liquid secondary antibody-labeled conjugate further may include buffers, salts, detergents such as Triton X-100, surfactants such as Tween-20, and blocking proteins such as bovine serum albumen to provide for the elimination of non-specific binding of the stabilized conjugate to the membrane and for clearing the background without the user of additional buffers.

Figure 6:
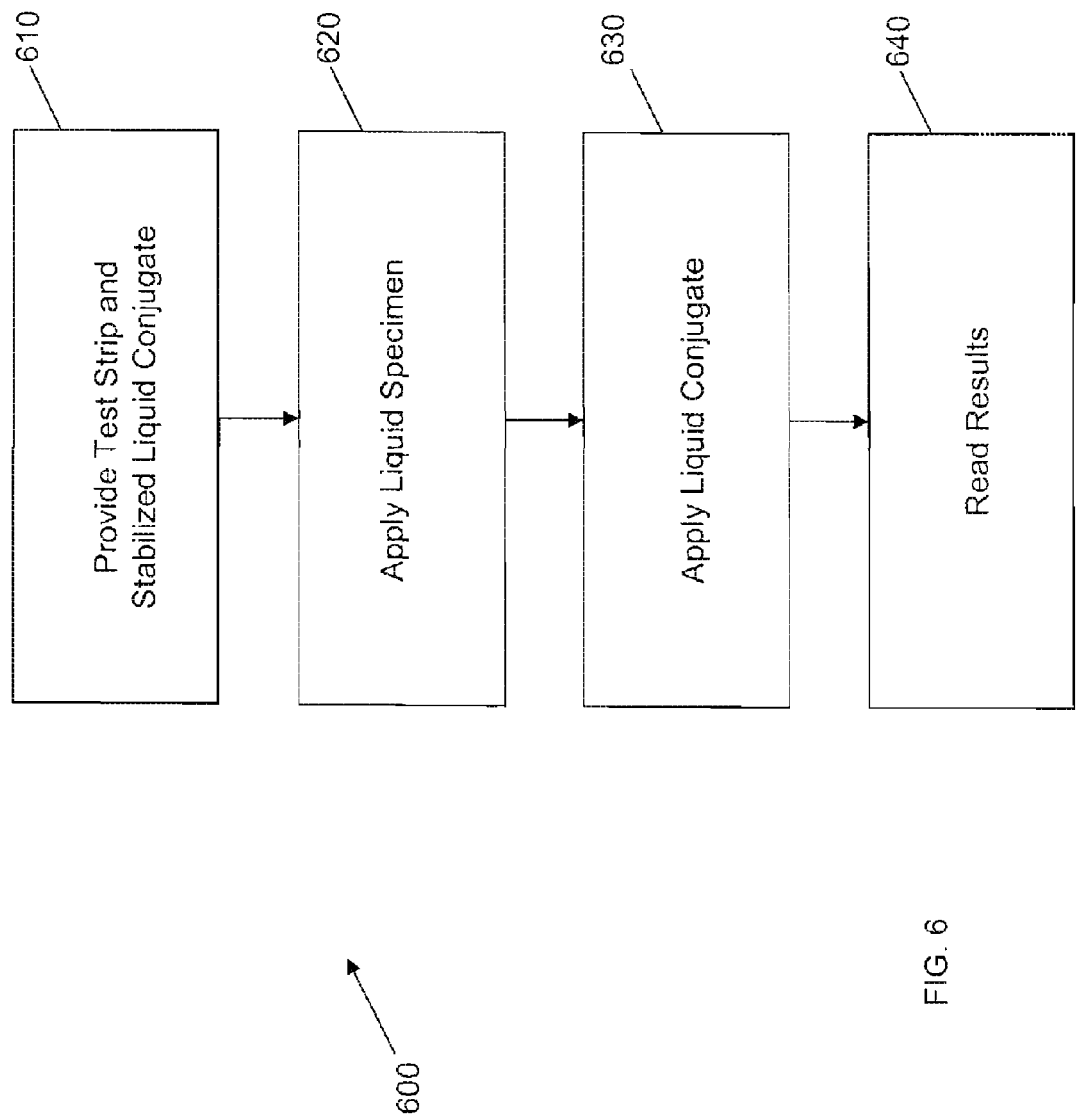
FIG. 6 is a flow chart illustrating a sequential solid phase immunoassay in accordance with the invention.

A sequential chromatographic immunoassay generally designated 600 is shown in FIG. 6. In a first step 610 the sequential solid phase immunoassay system is provided including the test strip 100 and the stabilized liquid conjugate. A fluid specimen including an analyte of interest is next applied to the specimen application zone 150 in a step 620. Preferably, an amount between 5 and 10 micro liters is applied.

In a case where the test strip 100 is disposed in the housing 300, the fluid specimen is applied through the specimen application window 415. The fluid specimen will then travel laterally toward the capture zone 140 in the direction indicated by the arrow (FIG. 1). If the analyte of interest is present in the fluid specimen, it will bind to the immobilized antigen at the capture zone 140.

In a third step 630, the liquid conjugate is applied to the absorbent material 115 distally of the fluid specimen. The liquid conjugate acts first to push the fluid specimen laterally toward the capture zone 140 and then to bind to the antibody in the fluid specimen captured in the capture zone 140. The binding of the liquid conjugate to the antibody may be indicated by a color such as red when colloidal gold is used for the conjugate. In the case where the test strip 100 is disposed in the housing 300, the liquid conjugate is applied by filling the well 420. In a final step 640, the results of the immunoassay are read.

Figure 7:
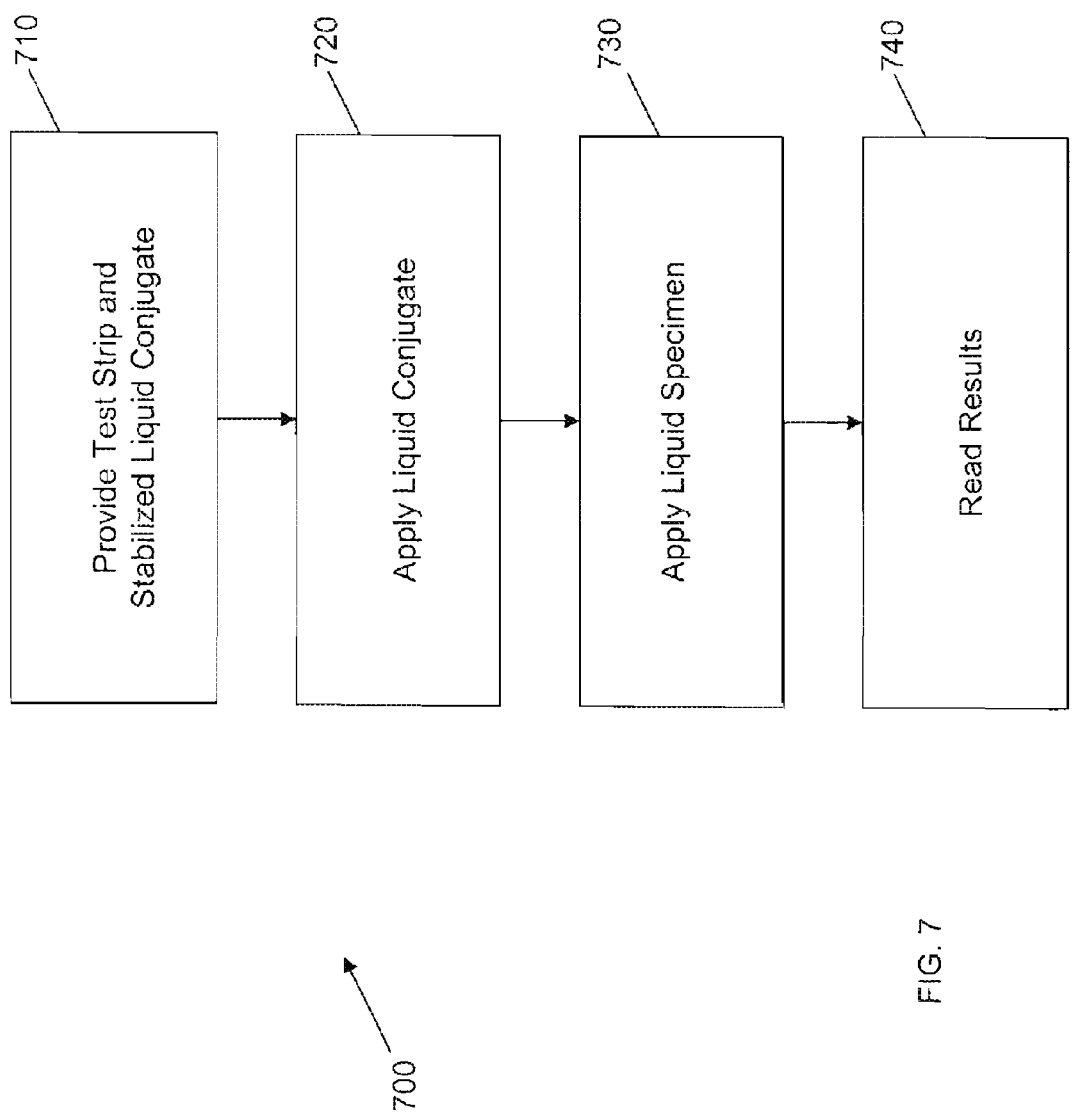
FIG. 7 is a flow chart illustrating an alternative sequential solid phase immunoassay in accordance with the invention.

In another aspect of the invention and with reference to FIG. 7, a sequential solid phase immunoassay generally designated 700 includes a first step 710 in which the solid phase immunoassay system is provided. The liquid conjugate is next applied to the absorbent material 115 in a second step 720. The applied liquid conjugate travels laterally toward the capture zone 140 in the direction indicated by the arrow (FIG. 1). Immediately after the second step 720, the fluid specimen including the analyte of interest is applied to the specimen application zone 150 in a third step 730. The fluid specimen will then travel laterally toward the capture zone 140 in the direction indicated by the arrow.

A first portion of the liquid conjugate facilitates the lateral migration of the fluid specimen toward the capture zone 140 by diluting the specimen to lower its viscosity and by carrying the fluid specimen along the test strip 110. If the analyte of interest is present in the fluid specimen, it will bind to the immobilized antigen at the capture zone 140. A second portion of the stabilized liquid conjugate arriving at the capture zone 140 following the first portion, binds to the antibody in the fluid specimen captured in the capture zone 140 and may be indicated by a red color in the case where gold is used for the conjugate. In a final step 740, the results of the immunoassay are read. Sequential solid phase immunoassay 700 may be performed when the test strip 100 is disposed in the housing 300 as will be apparent to one of ordinary skill in the art.

Figure 8:
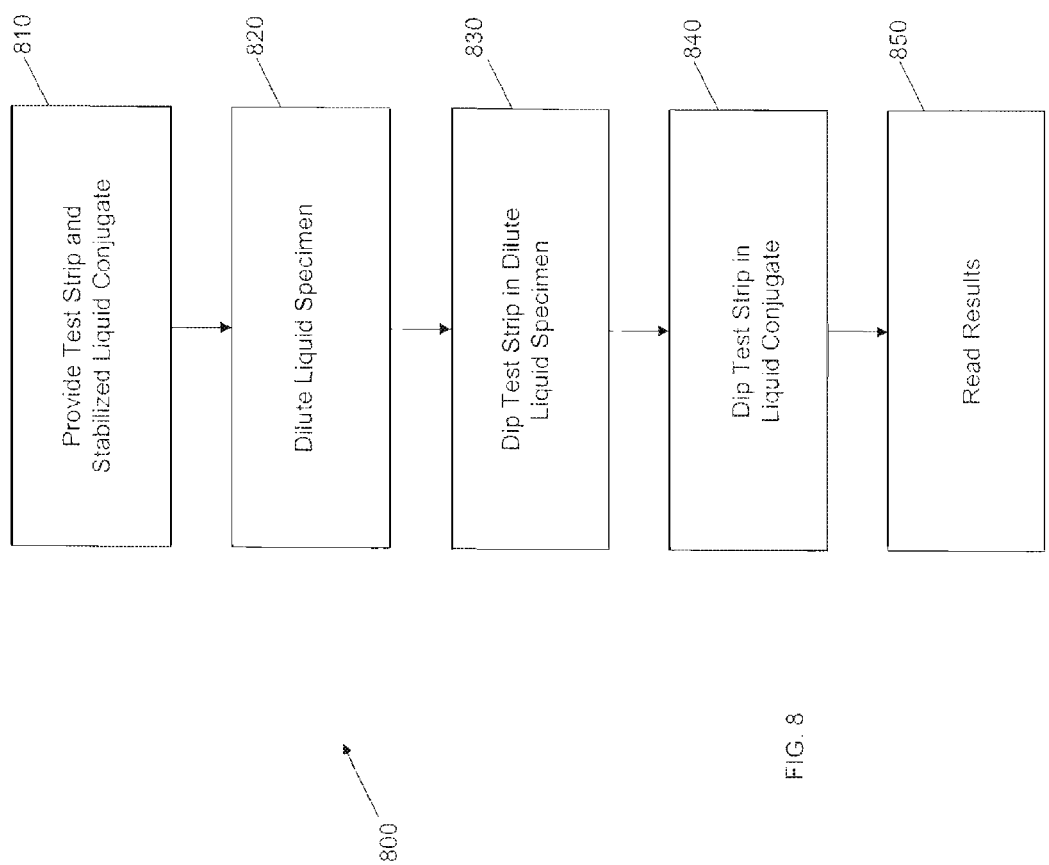
FIG. 8 is a flow chart illustrating an alternative sequential solid phase immunoassay in accordance with the invention.

In yet another aspect of the invention and with reference to FIG. 8, a sequential solid phase immunoassay generally designated 800 includes a step 810 in which the solid phase immunoassay system is provided. In a step 820 the fluid specimen including the analyte of interest is mixed with a buffer or the stabilized liquid conjugate to dilute the fluid specimen. Steps 810 and 820 may be performed in any order. In a third step 830, the test strip 100 is dipped in the dilute fluid specimen such that the absorbent material 115 is soaked thereby. The dilute fluid specimen will then travel laterally toward the capture zone 140 in the direction indicated by the arrow (FIG. 1). The diluent, either the buffer or the liquid conjugate, facilitates the lateral migration of the fluid specimen by lowering its viscosity and by carrying the fluid specimen along the test strip 110. If the analyte of interest is present in the fluid specimen, it will bind to the immobilized antigen at the capture zone 140. In a fourth step 840, the test strip 100 is dipped in the liquid conjugate such that the absorbent material 115 is soaked thereby. The liquid conjugate then travels laterally toward the capture zone 140 in the direction indicated by the arrow. The liquid conjugate acts to push the fluid specimen laterally toward the capture zone 140. The liquid conjugate arriving at the capture zone 140 binds to the antibody in the fluid specimen captured in the capture zone 140 and may be indicated by a red color in the case where gold is used for the conjugate. In a final step 850, the results of the immunoassay are read.

Exemplary analytes include human or animal antibodies detectable in specimens having viruses; bacteria; Chlamydiae; fungi; food, environmental and other allergens; autoimmune antigens; drugs; and organic and inorganic chemicals.

Exemplary detection/visualization reagents include class/species specific antibodies adsorbed or chemically bonded to colloidal metal such as gold, latex particles, dyes, and fluorogens.

The sequential chromatographic immunoassay and system of the invention advantageously provide a visualization reagent that combines a detection component such as the labeled secondary antibody conjugate and clearing components in one reagent to be used as a single solution. The immunoassays disclosed ensure that a sufficient and constant supply of the visualization reagent is applied to the test strip throughout the test run time. The first and second portions of the visualization reagent migrate in the same direction as, and behind, the fluid specimen to thereby provide a sequential reaction. The visualization reagent is not exhausted in binding to extraneous non-specific antibodies left by the fluid specimen such as serum on the path to the capture zone and no Hook effects can occur. The detection reaction may continue for as long as desired or as necessary to obtain a sensitive a result. The sequential solid phase immunoassay and system of the invention further provide universal visualization reagents that can be used for all serological tests within a class. The sequential solid phase immunoassay and system of the invention further do not require wash or blocking buffers at the initiation of the specimen addition, or between steps of sample addition and visualization reagent addition, or at the termination of the reaction.

It is apparent that the above embodiments may be altered in many ways without departing from the scope of the invention. For example, the system and method of the invention may be used to resolve any dispute between community members. Further, various aspects of a particular embodiment may contain patentably subject matter without regard to other aspects of the same embodiment. Still further, various aspects of different embodiments can be combined together. Accordingly, the scope of the invention should be determined by the following claims and their legal equivalents.

What is claimed is:

1. A method of performing a sequential solid phase immunoassay comprising the steps of:
    a) providing a sequential solid phase immunoassay system including a test strip having a first absorbent material disposed at a first end thereof and a second absorbent material disposed at a second end thereof, a fluid specimen application zone disposed between the first and second absorbent materials and proximate to the first absorbent material, an antigen immobilized on the test strip at a capture zone, the capture zone disposed between the first and second absorbent materials and distally of the first absorbent material;
    b) applying a stabilized liquid secondary antibody conjugate to the first absorbent material, wherein said stabilized liquid secondary antibody conjugate flows towards the capture zone and through the fluid specimen application zone;
    c) applying a fluid specimen to the fluid specimen application zone immediately after said application of the secondary antibody conjugate to the first absorbent material, wherein said fluid specimen application zone is in the path of said flow of said stabilized liquid secondary antibody conjugate, wherein said fluid specimen is applied onto said flow of said stabilized liquid secondary antibody conjugate, and wherein said flow of said stabilized liquid secondary antibody conjugate carries the applied fluid specimen to the capture zone; and
    d) reading the results at the capture zone.

2. The method of performing a sequential solid phase immunoassay of claim 1, wherein the stabilized liquid secondary antibody conjugate comprises an excess of labeled secondary antibody conjugate, buffers, salts, detergents, surfactants, and blocking proteins.

* * * * *